US00RE38684E

(19) United States
(12) Reissued Patent
Cesarone

(10) Patent Number: US RE38,684 E
(45) Date of Reissued Patent: Jan. 4, 2005

(54) FREELY SEPARABLE SURGICAL DRILL GUIDE AND PLATE

(75) Inventor: Morris D. Cesarone, Linwood, MA (US)

(73) Assignees: Synthes AG Chur, Chur (CH); Synthes (USA), Paoli, PA (US)

(21) Appl. No.: 09/686,198

(22) Filed: Oct. 10, 2000

Related U.S. Patent Documents

Reissue of:
(64) Patent No.: 5,851,207
Issued: Dec. 22, 1998
Appl. No.: 08/886,547
Filed: Jul. 1, 1997

(51) Int. Cl.[7] ..... A61B 17/80
(52) U.S. Cl. ..... 606/69; 606/96
(58) Field of Search ..... 606/80, 96, 97, 606/98, 70, 71, 190, 198; 408/241 G, 200

(56) References Cited

U.S. PATENT DOCUMENTS

| | | | | |
|---|---|---|---|---|
| 1,831,813 | A | 11/1931 | Levedahl | |
| 2,248,054 | A | 7/1941 | Becker | 145/52 |
| 2,490,364 | A | 12/1949 | Livingston | 128/92 |
| 2,494,229 | A | 1/1950 | Collison | 128/92 |
| 2,839,953 | A | 6/1958 | Hanger | 77/13 |
| 2,935,905 | A | 5/1960 | Winslow | 77/55 |
| 3,760,802 | A | 9/1973 | Fischer et al. | 128/92 |
| 4,119,092 | A | 10/1978 | Gil | 128/92 D |
| 4,312,337 | A | 1/1982 | Donohue | 128/92 |
| 4,341,206 | A | 7/1982 | Perrett et al. | 128/92 EB |
| 4,360,012 | A | 11/1982 | McHarrie et al. | 128/92 EB |
| 4,465,065 | A | 8/1984 | Gotfried | 128/92 BB |
| 4,537,185 | A | 8/1985 | Stednitz | 128/92 |
| 4,570,624 | A | 2/1986 | Wu | 128/92 EB |
| 4,599,999 | A | 7/1986 | Klaue | 128/92 EB |
| 4,716,893 | A | 1/1988 | Fischer et al. | 128/92 |
| 4,760,843 | A | 8/1988 | Fischer et al. | 128/92 |
| 4,788,970 | A | 12/1988 | Kara et al. | 128/92 ND |
| 4,805,634 | A * | 2/1989 | Ullrich et al. | 606/198 |
| 4,903,691 | A | 2/1990 | Heinl | 606/70 |
| 5,026,376 | A | 6/1991 | Greenberg | 606/96 |
| 5,133,720 | A | 7/1992 | Greenberg | 606/96 |
| 5,147,367 | A | 9/1992 | Ellis et al. | 606/96 |
| 5,151,103 | A | 9/1992 | Tepic et al. | 606/69 |
| 5,154,721 | A | 10/1992 | Perez | 606/117 |
| 5,364,399 | A | 11/1994 | Lowery et al. | 606/69 |
| 5,409,493 | A | 4/1995 | Greenberg | 606/96 |

(List continued on next page.)

FOREIGN PATENT DOCUMENTS

GB 2 243 316 A 10/1991

OTHER PUBLICATIONS

"The Standard Cervical Spine Locking Plate System", Synthes® Spine catalog, 1995.

"Cervical Spine Locking Plate", Synthes® Spine catalog, 1991.

*Primary Examiner*—Julian W. Woo
(74) *Attorney, Agent, or Firm*—Jones Day

(57) ABSTRACT

Instrumentation for osteofixation including a locking bone plate and a surgical drill guide. The plate has a plurality of fastener holes with inner walls of a preselected hole diameter. The drill guide has a guide member, for guiding a drill bit, and a hollow collet disposed substantially coaxially with the guide member. A radially expandable forward end of the collet comprises a radially expandable neck and an outwardly projecting rim disposed forward of the neck. This rim defines a contracted outer rim diameter that is smaller than the hole diameter in a contracted collet position, and an expanded outer rim diameter that is larger than the hole diameter in an expanded position. Thus, the rim is freely extractable through the plate hole in the contracted position, but is unreceivable through the plate hole in the expanded position. The collet neck is configured and dimensioned to press outwardly against an inner wall of the plate hole when the neck is expanded.

25 Claims, 7 Drawing Sheets

U.S. PATENT DOCUMENTS

| | | | | |
|---|---|---|---|---|
| 5,423,826 | A | 6/1995 | Coates et al. | 606/96 |
| 5,425,490 | A | 6/1995 | Gobble et al. | 227/175 |
| 5,429,641 | A | 7/1995 | Gotfried | 606/67 |
| 5,437,677 | A | 8/1995 | Shearer et al. | 606/96 |
| 5,489,210 | A | 2/1996 | Hanosh | 433/173 |
| 5,507,801 | A | 4/1996 | Gisin et al. | 606/86 |
| 5,520,690 | A | 5/1996 | Errico et al. | 606/61 |
| 5,531,746 | A | 7/1996 | Errico et al. | 606/61 |
| 5,676,666 | A | 10/1997 | Oxland et al. | 606/61 |
| 5,755,721 | A | 5/1998 | Hearn | 606/96 |

* cited by examiner

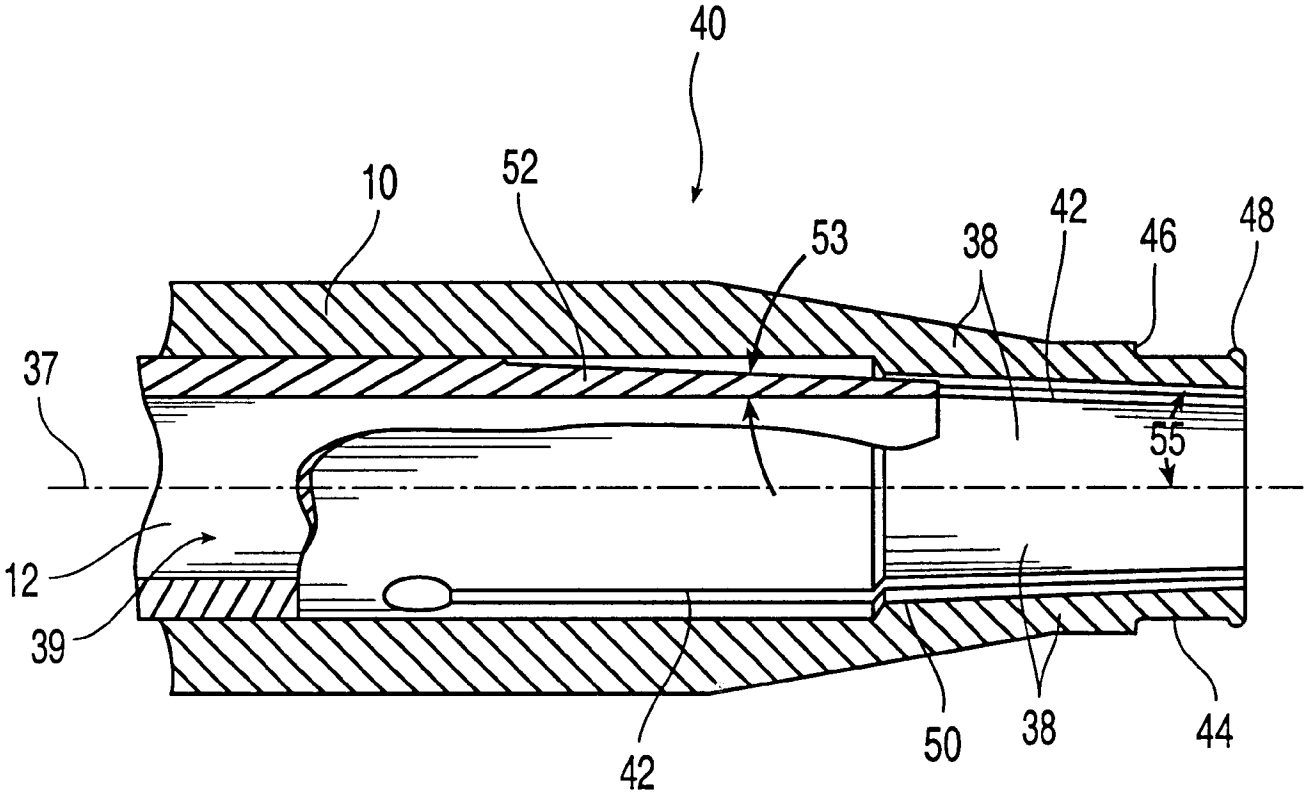
Fig. 2
(Amended)

FREELY SEPARABLE SURGICAL DRILL GUIDE AND PLATE

Matter enclosed in heavy brackets [ ] appears in the original patent but forms no part of this reissue specification; matter printed in italics indicates the additions made by reissue.

TECHNICAL FIELD

The present invention relates to a surgical drill guide and a surgical plate that are attachable to each other for retaining a precise alignment therebetween. More particularly, the invention relates to a bone plate with a fastener hole and surgical drill guide with an expandable collet having a rim that, when contracted, is smaller than the fastener hole.

BACKGROUND OF THE INVENTION

Surgical fixation plates are used in many procedures to mend, align, and alter compression of patients' bones. These plates are primarily secured to the patient's bones by a plurality of fasteners such as screws. Proper orientation and alignment of fasteners and secure surgical fixation of the plates is crucial to avoiding future complications after implantation. This is especially the case for cervical spine locking-plates, such as sold by SYNTHES Spine. These plates are used for long term, intravertebral fixation, bone-fragment fixation, and anterior decompression in the cervical region of the spine. Locking plates enable secure mono-cortical implantation, meaning that their screws need only penetrate the anterior bone cortex. In conventional plates, screws must pass through both the anterior and posterior bone cortices to attain sufficient support. In passing through both cortices, conventional plates risk penetrating the spinal chord.

Surgeons implanting vertebral plates operate within a fine margin of error. Fairly little vertebral bone is available for setting fasteners. Each plate hole should coaxially align with its screw, i.e., each plate hole has an axis that must align with the screw axis. Otherwise, screws do not seat correctly with the plate. Thus, misalignments can potentially damage tissues, including the spinal cord, or lead to improperly secured plates.

Locking plates in particular demand precise fastener alignment. Cervical locking plates are generally about 2 mm thick. Some screw holes in these plates are inclined by 12° to the surface of the plate to permit optimal screw placement in the cervical region of the spine.

Anchor screws secure the locking plate to the vertebral body. Anchor screws have hollow, longitudinally slotted expansive heads that must fit snugly within a plate's screw hole. These screws are externally threaded to secure to the vertebral bone and the plate. These screws are also threaded internally from their head through a shallow portion of their shaft. Once a surgeon implants an anchor screw, he or she screws a small locking screw into the head of the anchor screw. This locking screw expands the head of the anchor screw so that the head presses outwardly against the locking plate's hole for a compression fit. This compression fit locks the screw in place and creates a solid coupling between the plate and the screw, preventing motion between them and preventing the screw from backing out from the plate, which may damage the esophagus.

This locking mechanism demands extremely precise screw alignment. If the holes drilled in the bone prior to anchor screw insertion are misaligned or off center, anchor screws and locking-plate holes will not seat correctly. Forcing a misaligned anchor screw into the plate hole can collapse the expansive head and prevent insertion of a locking screw. Thus, accurate drill guides for use in drilling the screw hole into the bone are critical to successful operations.

Known drill guides for locking plates, such as disclosed in a SYNTHES Spine catalog dated 1991, are generally a cylindrical tube shaped to receive and guide a drill bit. Most known guides also have a handle. A tip of the tube is shaped to slide into screw holes. A shoulder near the guide tip rests against a modest countersink in the screw hole to limit the guide's insertion into the hole. Constant axial pressure against the plate is required to maintain the guide in the hole, although it is sometimes beneficial to limit unnecessary pressure against the spine during drilling. Also, a clearance between the tip of the guide and the hole is provided to ease insertion into the hole. Due to this clearance, the diminutive thickness of the plate, and the small size of the countersink, an amount of angular play exists in this system. Other similar guides, though shown with femur fixation-plates, are disclosed in U.S. Pat. Nos. 2,494,229, and 5,417,367.

A more accurate drill guide is sold by SYNTHES Spine and shown in its catalog dated 1995, in which angular play is reduced and which does not require a constant force against the plate. This drill guide has an expanding collet formed with a plurality of fingers disposed coaxially about a drill guide sleeve. The sleeve is conical, and when it is slid forward, it spreads the collet fingers to lock them against the inside walls of a screw hole in a cervical spine locking plate. A scissoring handle linked to the collet and the sleeve controls the relative forward and backward motion therebetween.

At the forward tip of the drill guide, the collet has a neck, designed to press against the inside walls of the screw hole. Adjacent this neck is a radially extending rim, which, in a naturally assumed contracted position, has a diameter slightly larger than the screw hole, providing an interference fit. As a surgeon inserts the tip of the collet into the screw hole, the greater diameter of the rim provides a surgeon with a detectable snap and decreased resistance to insertion of the collet as the rim passes to the far side of the hole. To extract the collet from the screw hole, the surgeon must apply a slight force to pry the rim back through the smaller diameter walls of the hole, as these force the rim to contract to the smaller diameter.

A problem frequently arises when using this drill guide during surgery. Once the plate has been carefully positioned in the desired implantation position within the incision, when the surgeon attempts to remove the drill guide from the bone plate, the collet rim often catches on the plate. This catching prevents the drill from releasing the plate, and the surgeon often pulls the plate out of the incision along with the drill guide. As a result, any temporary fixation pins that were holding the plate to the bone could be stripped out of the vertebra, weakening the supporting bone structure, or in the best scenario, the plate would merely become misaligned with previously drilled holes. Even if the plate only becomes misaligned, however, careful realignment of the plate is required before the implantation procedure can continue.

Due to the precise nature of the relationship between the dimensions of screw hole and the rim and neck of the collet, the above problem cannot be avoided by simply using a particular drill guide in combination with any available plate that has larger screw holes. The drill guide and its corresponding locking plates are precisely size-matched and are sold in kits. A drill guide of this type cannot adequately lock and function as a guide with available plates with differently sized holes than those for which the guide was designed. Slightly large holes, for instance, permit excessive play between the plate and the guide, even when the guide is expanded.

Thus, a drill guide is needed that can disengageably lock to a surgical plate fastener hole, but without catching as the drill guide is extracted therefrom.

SUMMARY OF THE INVENTION

The invention is directed to instrumentation for fixing bones or bone fragments to each other. The instrumentation includes a bone plate for attaching to the bones, and a drill guide. The bone plate has at least one fastener hole through which fasteners, such as locking bone screws, fasten the plate to the bones. The hole has an inner wall with a predetermined hole diameter.

The drill guide has a guide member for guiding a drill bit. A hollow collet disposed coaxially with the guide member has a radially expandable forward end with a neck and outwardly projecting neck and an outwardly projecting rim forward of the neck. The neck is configured to press outwardly against an inner wall of the plate hole when collet is in the expanded position. The rim is freely extractable through the plate hole when the collet is in a contracted position. However, when the collet is in an expanded position, the rim does not fit through the plate hole.

To achieve this, the rim defines a contracted outer rim diameter smaller than the hole diameter when the rim is in a contracted position, rendering the rim freely extractable from the hole. When the rim is in an expanded position, it defines an expanded outer rim diameter larger than the hole diameter, rendering the rim impassable through the plate hole. The contracted rim diameter is preferably between 0.1 mm and 0.3 mm smaller than the hole diameter, or about 95% of the hole diameter. In the preferred embodiment, the rim protrudes radially from the neck by less than 0.1 mm. In one embodiment, the diameter of the rim is equal to that of the neck.

To further facilitate extraction of the rim from the hole, the rim has a rounded cross section in a plane extending through the axis of the neck and rim, preventing the rim from catching on the plate during its extraction therefrom. Also, a surface of the rim substantially adjacent the neck and configured at a first angle thereto of preferably less than about 55°, and more preferably of about 45°.

The guide member includes a guide sleeve movably axially and telescopically received within the collet. The sleeve defines a guide bore through which it axially receive and guide a drill bit. In a forward position within the collet, the sleeve biases the collet towards the expanded position. Preferably, the sleeve has a surface tapered inwardly at a second angle of between 3° and 5° to its axis to effect the expansion of the collet. More preferably this taper angle is about 4°.

As a result, the invention provides a surgical drill guide and a bone plate that are securable to one another, but which do not catch on each other upon drill guide extraction. The guide is unfetteredly and freely removable from the plate.

BRIEF DESCRIPTION OF THE DRAWINGS

FIG. 2 is a cross-section, cutaway view of an expandable collet in a contracted position and a guide sleeve according to the invention;

DETAILED DESCRIPTION OF THE PREFERRED EMBODIMENT

Figure 1:
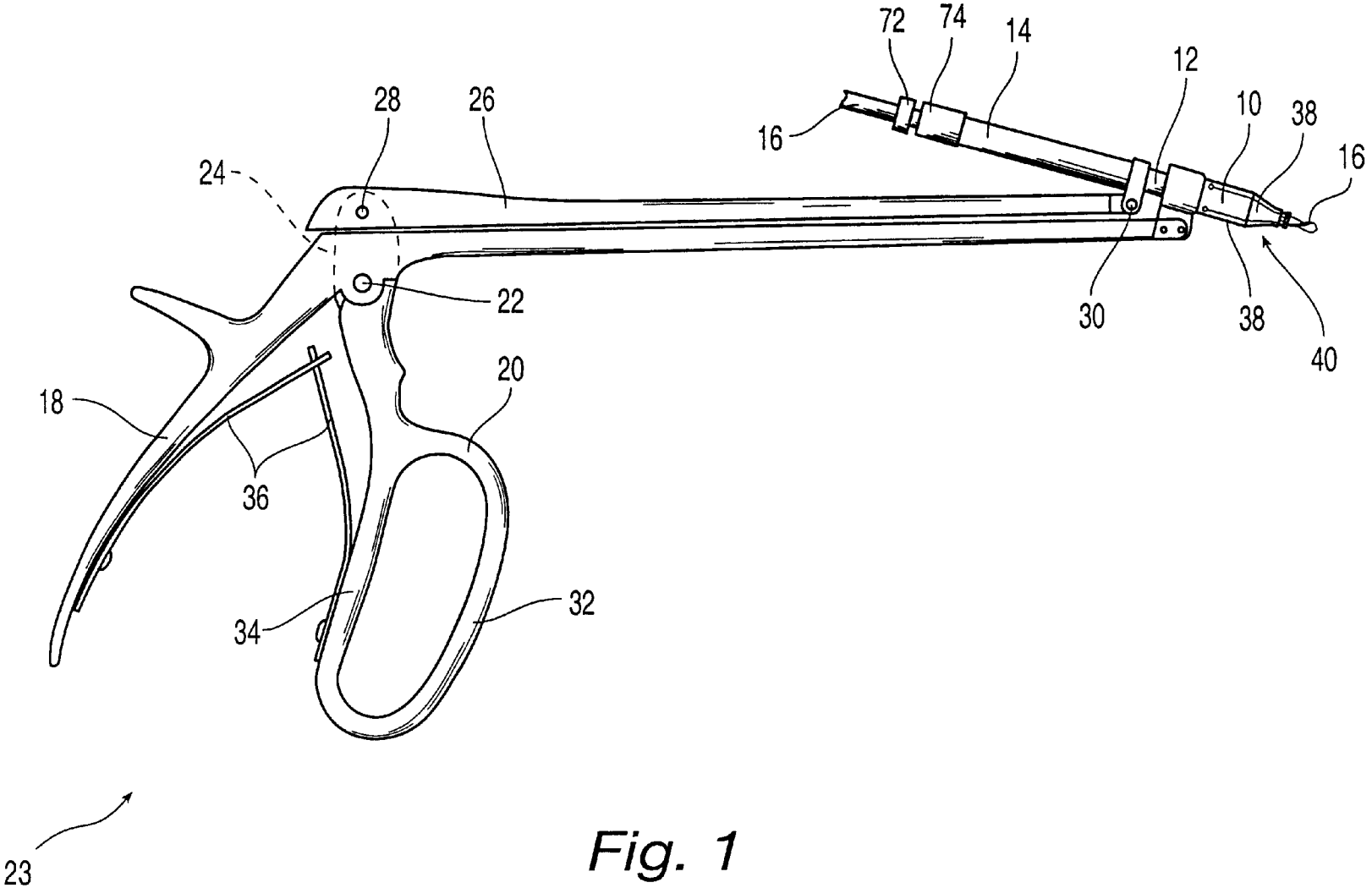
FIG. 1 shows a side view of a surgical drill guide according to the invention.

FIG. 1 shows an embodiment of a surgical drill guide assembly 8 according to the invention, which is adapted for use with a cervical spine locking plate. At a forward end of the drill guide assembly is a collet 10. Telescopically and slideably engaged within collet 10 is a guide sleeve 12. Preferably, a tissue protector 14 extends rearwardly from the sleeve 12. The collet 10, sleeve 12, and tissue protector 14 are adapted to axially receive a drill bit 16, and the guide sleeve 12 is sized to retain the spinning bit 16 in a precise coaxial alignment.

The collet 10 is fixed to a remote rear handle-member 18. The handle member 18 is pivotably attached to a scissor grip 20 by a handle pin 22. Together, handle member 18 and scissor grip 20 form a drill guide assembly handle 23, which allows a user to maneuver and use the drill guide assembly. The scissor grip 20 has an arm 24 that extends to the opposite side of the handle pin 22 from the grip 20 to pivotably attach to an actuation bar 26 at actuation pin 28. An end of the bar 26 is pivotably attached with the sleeve 12 at sleeve pin 30.

Thus, the entire drill guide assembly in this embodiment forms a four bar linkage. When a surgeon squeezes scissor grip 20 towards handle member 18, the arm 24 forces the actuation bar 26 forward. This in turn forces the sleeve 12 to slide forward, deeper into collet 10. Preferably, however, no part of the sleeve 12 can slide further forward than the front of the collet 10. The scissor grip 20 has a forward wall 32 and a rear wall 34 to help the surgeon manually force the sleeve 12 forward or backward by closing or opening the guide sleeve assembly with only one hand. Preferably, leaf springs 36 are fastened to the handle member 18 and the scissor grip 20 to further assist rearward motion of the sleeve 12 by biasing the handle 23 towards an open position.

The collet 10 has a forward end 40 that is radially expandable. In this embodiment, the collet has a plurality of fingers 38 that can be spread apart to expand the forward end 40 of the collet 10.

Referring to FIG. 2, the collet 10 coaxially receives the sleeve 12 about an axis 37. Also, a guide bore 39 extends along axis 37 for guiding a drill bit coaxially therein.

The forward end 40 of collet 10 is preferably comprised of longitudinally extending fingers 38. The fingers 38 are divided by slots 42 extending longitudinally between adjacent fingers 38. These fingers 38 are resiliently biased inwardly and naturally assume an inward disposition when in a relaxed state and when the sleeve 12 is in the unlocked position, as shown in the figure. In the figure, a portion of the sleeve 12 has been cut away to better illustrate the slots 42.

At a frontmost portion of the expandable forward end 40 of the collet 10, the fingers 38 form a radially expandable circumferential neck 44. At the back end of and adjacent to neck 44 is a shoulder 46, and at the front end of and adjacent to neck 44 are protrusions that form a radially expandable rim 48. These portions of the collet 10, i.e., the neck 44, the shoulder 46, and the rim 44, are preferably a single piece of material of unitary construction, in the interest of minimizing the size of the drill guide that must be inserted into an incision.

Figure 3:
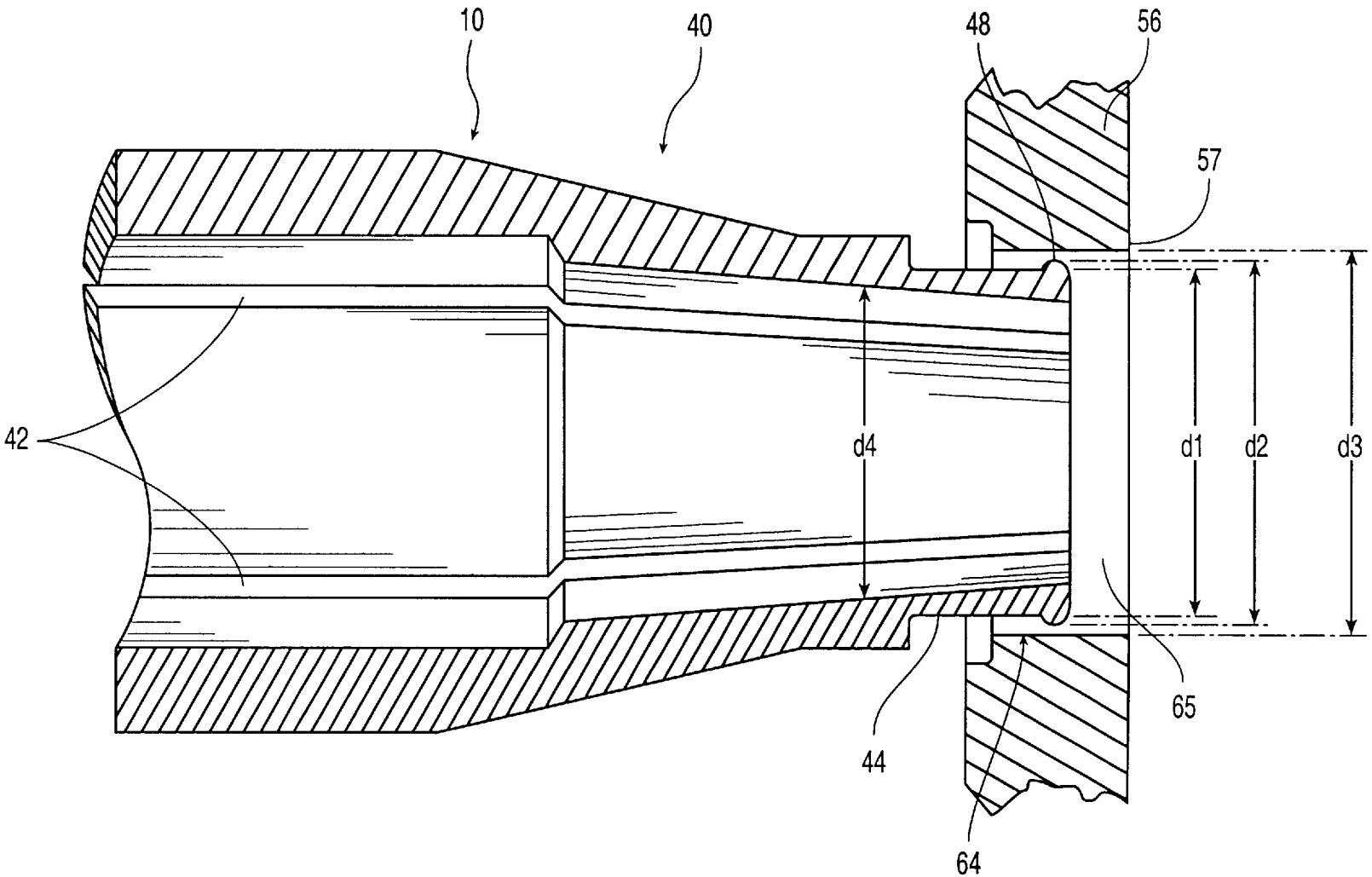
FIG. 3 is an enlarged cross-section of the collet being inserted into a locking plate.

In the contracted, unlocked position shown in FIG. 2, the neck 44 and the rim 48 are sized to fit freely through screw holes in a locking plate. FIG. 3 shows the collet 10 being inserted into a screw hole 64 in a locking plate 56. In the drawing, the collet is in its natural, contracted position. The collet 10 is resiliently biased towards this position, in which the neck 44 has a contracted diameter d1 and the rim has a contracted rim diameter d2. The screw hole 64 has an inner wall with a hole diameter d3.

The contracted rim diameter d2 is smaller than the hole diameter d3 to permit free and unfettered extraction of the rim 48 from the hole 64. Preferably, the contracted rim diameter measures between 0.1 mm and 0.3 mm less than the hole diameter d3. More preferably, the rim diameter d2 is 0.2 mm smaller than the hole. The contracted rim diameter d2 is preferably between 4.2 mm and 4.4 mm in a drill guide that functions with a hole diameter d3 of about 4.5 mm. Thus, the contracted rim diameter is approximately 95% the size of the hole diameter. Also, the contracted rim diameter d2 is preferably about between 1 mm and 2 mm larger than the contracted neck diameter d1. Thus, the rim 48 protrudes from the neck 44 by a preferred 1 mm. Hence, the contracted neck diameter d1 is preferably more than 95% as large as the contracted rim diameter d2.

These diameters permit a surgeon to extract, and most preferably also insert, the rim 48 of the collet 10 through a screw hole 64 without the rim 48 catching in the far side 57 of the plate 56 when the collet 10 is contracted. This arrangement virtually eliminates the possibility of collet 10 failing to disengage from a bone plate 56, reducing the likelihood of unintentional extraction of temporary fixation pins or misalignment of a previously positioned plate 56.

At the same time, having a rim 48, provides the surgeon with a detectable feel for when the rim has completely passed the through the hole 64. In alternative embodiments, the rim 48 may be eliminated completely, for instance by reducing the contracted rim diameter d2 to an equal size as the contracted neck diameter d1. These embodiments, though, would lack the signal to the surgeon produced by full passage of the rim 48 through the hole 64.

Figure 4:
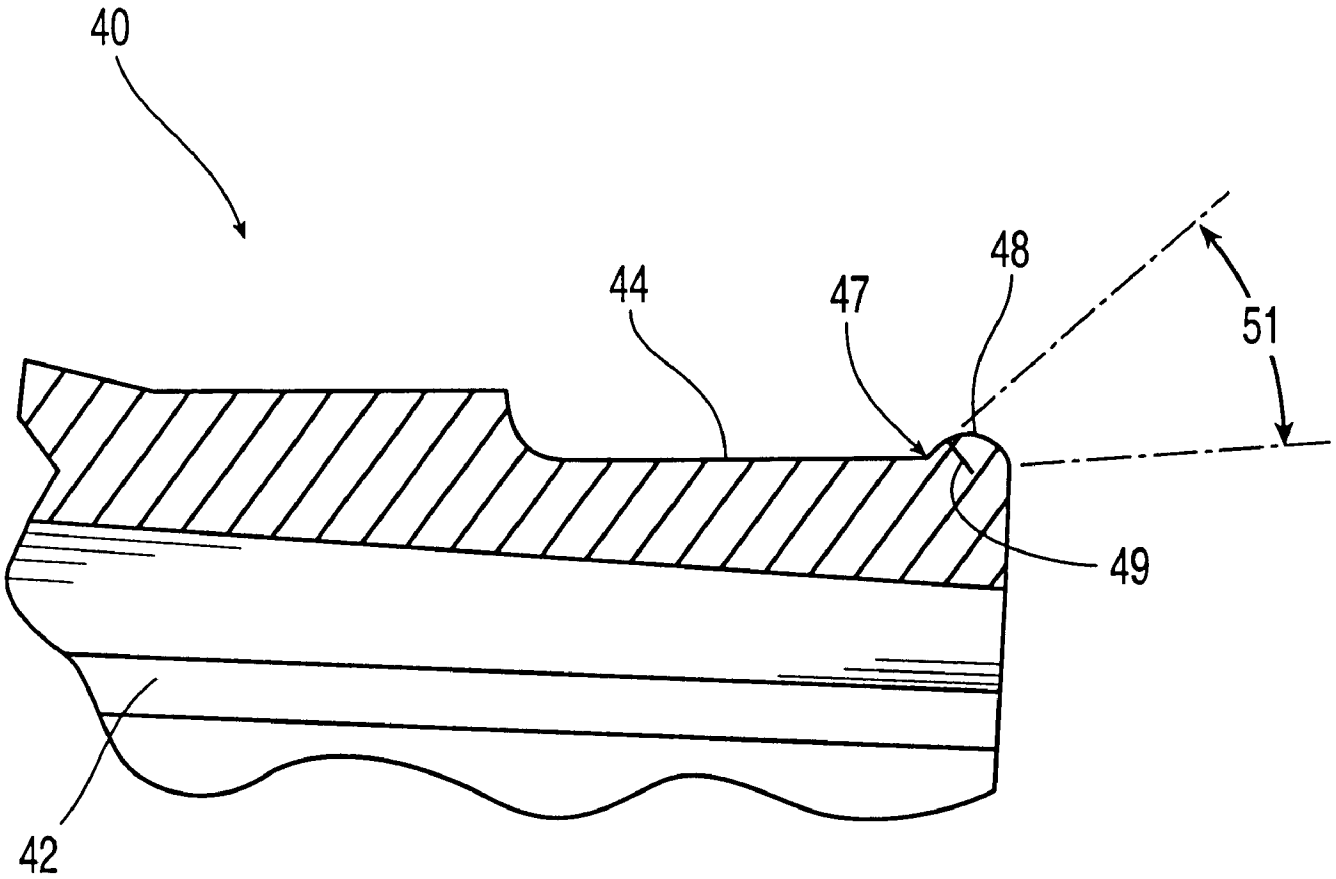
FIG. 4 is a further enlarged view of the front of the collet.

As shown in FIG. 4, to further foment free removal of the rim 48 from the hole 64, the rim 48 is rounded in a cross-section taken parallel to axis 37. The cross section preferably curves around a radius 49 of about 0.15 mm. Also, in this embodiment, a surface of the rim 48 disposed adjacent the neck 44 is configured at an angle 51 of less than 55° to the neck 44, and most preferably at about 45° thereto. In some embodiments, this angled surface is preferably joined to the neck 44 via a narrow surface 47 of concave radius.

Referring again to FIG. 3, shoulder 46 has a diameter d4 that is greater than the contracted rim diameter d2. Thus, the shoulder 46 has a diameter that is greater than the hole diameter d3 such that the shoulder 46 cannot be inserted therethrough. Still further, in the preferred embodiment, the neck 44 is slightly longer than the thickness of the hole wall 65, such that the neck can abut the wall of the locking plate hole and the rim 48 can abut the inside surface of a locking plate 56. In this manner, the drill guide assembly can be secured to the locking plate 56, restricting relative movement.

The inside of the expandable forward end 40 the collet 10 preferably has a variable inner diameter. Preferably, the fingers 38 have a step 50 or a taper, resulting in a smaller inner collet 10 diameter forward of the step 50.

The guide sleeve 12 includes a forward portion 52 that cooperates with the fingers 38 to expand the fingers 38 when the guide sleeve 12 is moved into a locked position. Preferably, the guide sleeve 12 is tapered at taper angle 53 to the axis 37 to form a conical forward portion 52. The conical section 52 of guide sleeve 12 pushes outwardly against the inner surface of the collet 10 as the guide sleeve 12 is moved forward to expand the forward end 40. In this embodiment, the conical section mates with and pushes against the inner collet 10 surface forward of step 50 to push the fingers 38 radially outward. When the guide sleeve 12 is in the unlocked position as shown in FIG. 2, the conical section 52 allows the fingers 38 to return to a relaxed, contracted position. This allows the collet 10 to be inserted and retracted from the plate hole. The taper angle 53 is preferably between 3° and 5°, and more preferably about 4°. The inner surface of the collet 10 forward of the step 50 is also preferably tapered at an angle 55 to axis 37 that is substantially equal to taper angle 53. This range of angles provides a desirable amount of movement of the sleeve 12 within the collet 10 to bias the collet 10 from a contracted position to an expanded position.

When the surgeon squeezes the handle 23, the guide sleeve 12 is moved forward and the conical section 52 cooperatively forces the inner surface of the collet 10 beyond step 50 and fingers 38 radially outward. Thus, the forward motion of the guide sleeve 12 towards a forward position expands the forward end 40 of the collet 10 to an expanded position. In this manner, the neck 44 can be expanded to abut the inner wall of the plate screw hole and the rim 48 is expanded to abut the inner surface of the locking plate. In the expanded position, the expanded outer diameter d5 of the rim 48 is greater than the plate hole diameter d3 so that the guide cannot be retracted from the plate hole, as shown in FIG. 6A.

Figure 5A:
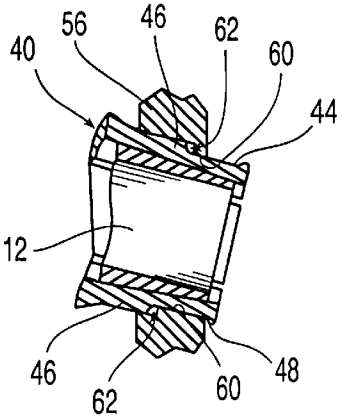
FIG. 5A is an expanded cross-section of the forward portion of the drill guide assembly of FIG. 3.
Figure 6A:
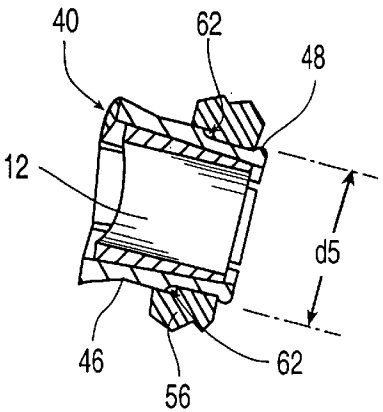
FIG. 6A is an expanded cross-section of the forward portion of the drill guide assembly of FIG. 4.
Figure 5:
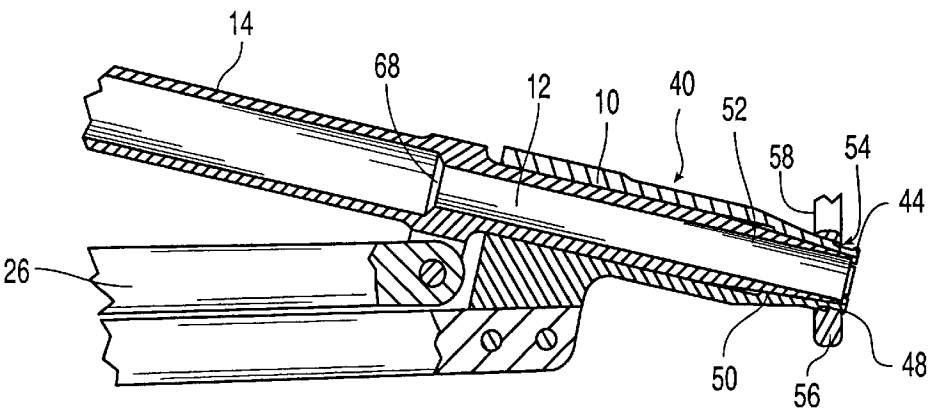
FIG. 5 is a cross-section of a drill guide assembly of the invention locked coaxially to a screw hole and aligned at an angle to the surface of a locking plate.
Figure 6:
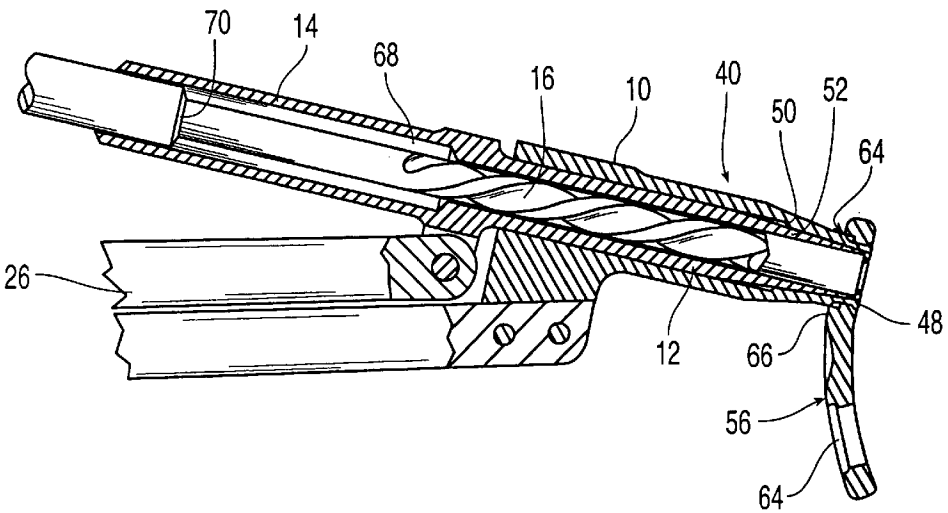
FIG. 6 is a cross-section of a drill guide assembly according to the invention locked coaxially to a screw hole extending perpendicularly to the surface of the locking plate.

FIGS. 5–6A show the sleeve 12 in a locked, forward position, and the expandable end 40 in an expanded position and locked to different screw holes of the same predetermined diameter d3. Referring to FIGS. 5 and 5A, screw hole 54 in locking plate 56 is disposed at an angle of about 12° to the locking plate's 56 outside surface 58. The drill guide assembly is configured so that when the collet 10 is expanded, as shown, the neck 44 presses outwardly against interior wall 60 of screw hole 54, positively gripping the wall 60. The rim 48 preferably abuts the back surface of the plate 56 so that the neck positions the guide. The shoulder 46, on the other hand, preferably does not abut the outside surface 58 of the plate 56. A firm locking against the plate 56 results, and precise co-axial alignment through the center of screw hole 54 is achieved even though the surface area of wall 60 is small. In this embodiment, the axis of the drill guide is aligned with the axis of the plate screw hole 54. Thus, the axis of the hole drilled into the bone will also be aligned with the axis of the plate screw hole 54. In this manner, an anchoring screw inserted into the drilled hole will be centered and aligned with the plate screw hole 54, i.e., they too will be substantially co-axially aligned.

The plate 56 and the guide may become slippery during use when blood and drilled tissue residue cover the instruments. In this situation, rim 48 aids in preventing the collet 10 from sliding backwards, out of the hole 54. The rim 48 is adapted to rest against the far side of the plate 56, near the perimeter of the hole 54. Note that when the drill guide of this embodiment is locked to an angled hole 54, as shown, only a segment of rim 48 may actually contact the back of the plate 56. This small contact surface suffices to retain the collet 10 within the hole 54.

Preferably, a gap 62 remains between the forwardly facing surface of shoulder 46 and the plate 56. This is because, in the preferred embodiment, the shoulder 46 is not necessary for achieving a proper drill alignment or a secure locking. Consequentially, a surgeon need not press the drill guide against the locking plate 56 to keep the guide properly seated within the hole 54.

FIGS. 6 and 6A show the same embodiment of the invention locked to a screw hole 64 in a different part of locking plate 56. Hole 64 is perpendicular to the locking plate's 56 surface 66. In this application, most of the rim 48 is in contact with the back of plate 56. Similarly to the applications shown in FIGS. 5 and 5A, a gap 62 preferably remains between the forwardly facing surface of shoulder 46 and the plate 56.

As seen in FIGS. 5 and 6, the internal diameter of the tissue protector 14 is preferably wider than that of the sleeve 12, forming a step 68. This step 68 may alternatively be formed in a different place along the length of the tissue protector 14 or the sleeve 12. Step 68 is adapted to stop a surgical drill bit 16 that is inserted through the rearward end of the tissue protector from advancing beyond a predetermined depth. This stopping action occurs when the step 68 contacts a portion 70 of the drill 16 that is wider than the internal diameter of the sleeve 12 or the tissue protector 14 forward of the step 68, as illustrated in FIG. 6.

Referring again to FIG. 1, the drill bit 16 illustrated has a safety stop 72 with a wider diameter than the interior of the tissue protector 14. The rear 72 of the tissue protector 14 also preferably prevents advancement of the drill bit 16 when the tissue-protector rear 74 contacts the bit's 16 safety stop 72. By selecting a bit 16 with an appropriately located safety stop 72 or safety step 68, the surgeon is assured that the bit 16 will penetrate the vertebral body no further than necessary for insertion of a screw.

Figure 7:
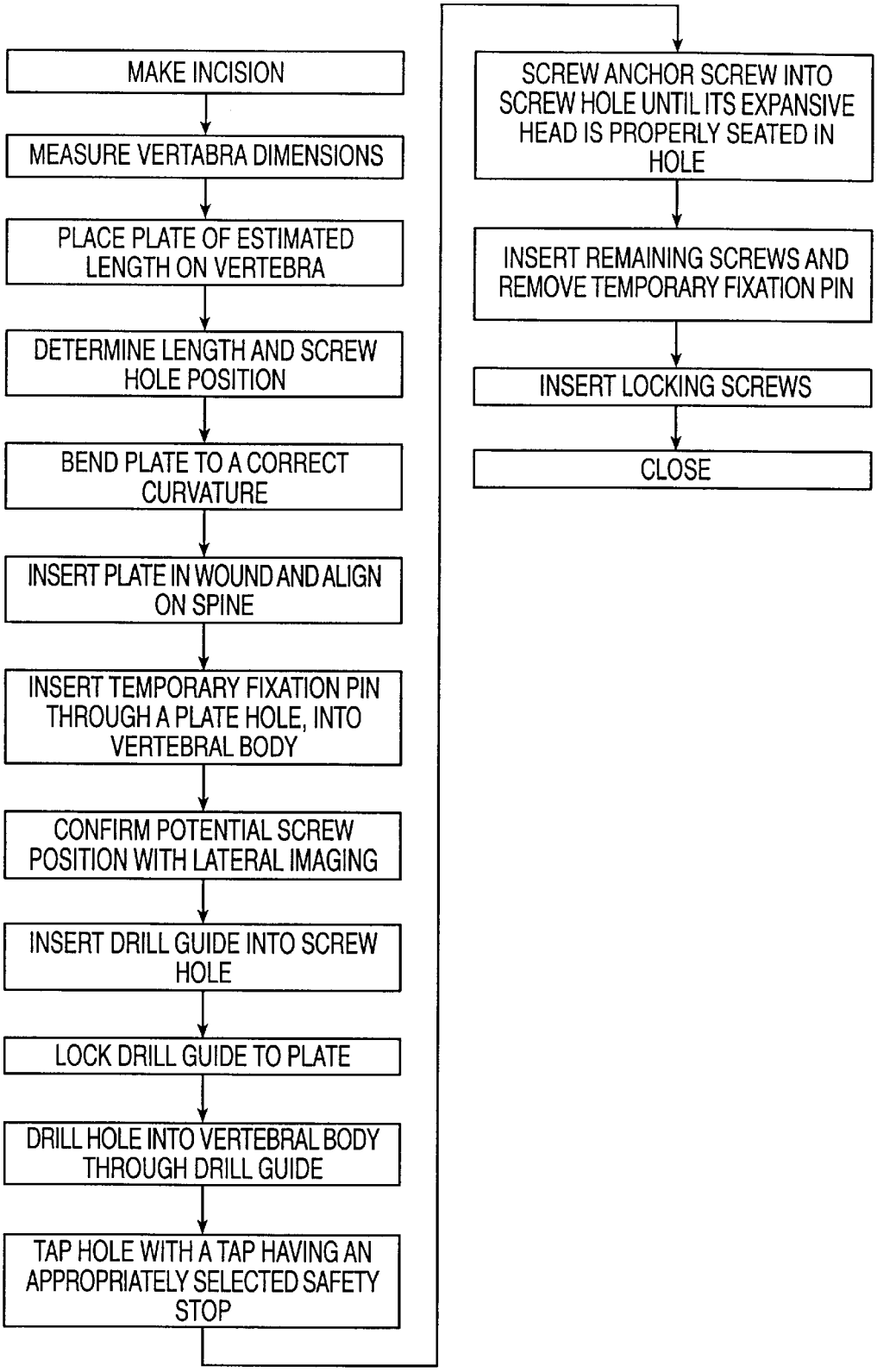
FIG. 7 is a flow chart of the method of implanting a cervical spine locking plate.

The flow chart in FIG. 7 provides the procedure for implanting a cervical spine locking plate. After making an incision, and measuring the cervical vertebra to be fixed with the plate, a surgeon places a cervical locking plate of a correct estimated length on the vertebral body. The surgeon then bends the plate to contour it to the correct lordotic curvature. Once the plate is properly positioned on the vertebra, it is secured with a temporary fixation pin, which is monitored under lateral imaging. The surgeon then locks the drill guide to the plate and drills into the bone. He or she then taps the hole, inserts an anchor screw, and inserts a locking screw to lock the anchor screw to the plate. The locking and drilling process is repeated for the remaining screws. The last hole is drilled through the plate hole in which the locking pin was located. Finally, the surgeon closes the wound.

Figure 8:
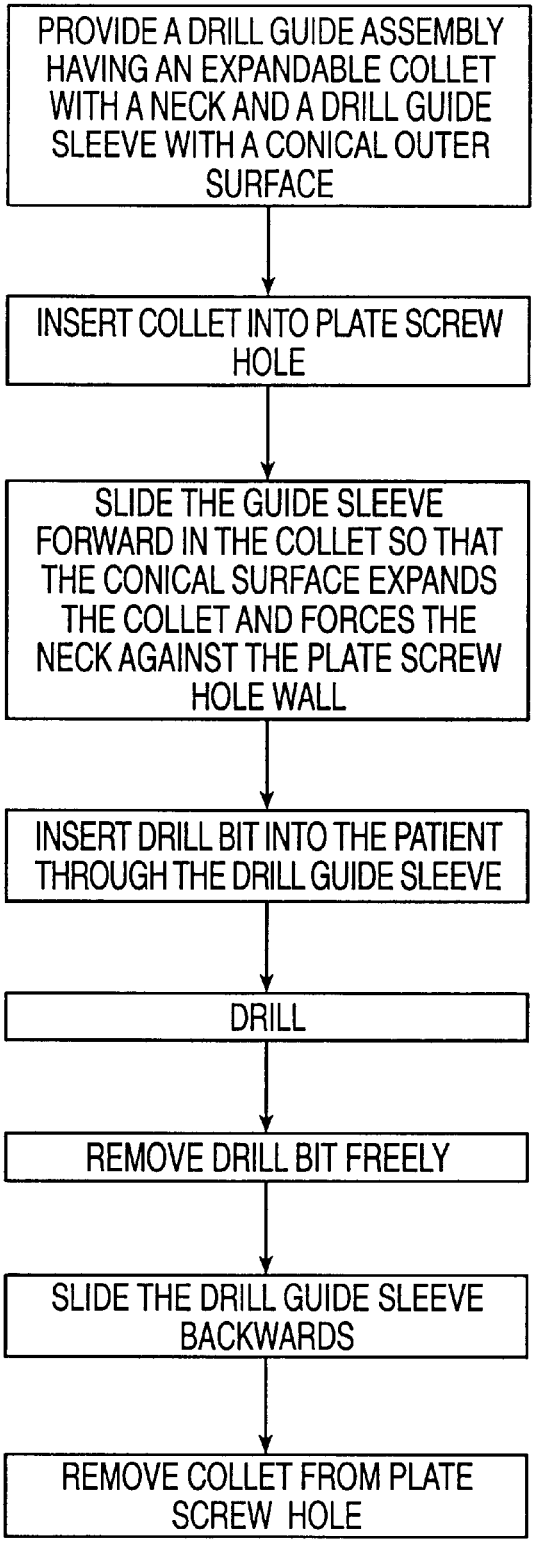
FIG. 8 is a flow chart of the method for using the drill guide assembly to drill an aligned hole.

The chart in FIG. 8 shows the procedure for using the drill guide. A surgeon inserts the collet into the plate screw hole and squeezes the handle to slide the sleeve forward, expanding the collet with the conical portion of the sleeve and locking the drill guide to the plate. The surgeon then inserts the drill through the drill guide sleeve, drills the hole, and removes the drill. He or she opens the handle of the drill guide, sliding the sleeve backwards and releasing the collet from the hole, and then freely and unfetteredly removes the guide from the plate.

Before and during locking-plate implantation, the surgeon may insert the expandable end 40 of the collet 10 into a screw hole in a locking plate 56. By squeezing the handle 23, the surgeon may grasp and manipulate the plate 56 without an additional plate holder if he or she so desires.

Preferably, friction between the forwardly moved conical portion 52 and the inner surface of fingers 38 beyond step 50 retains the expandable end 40 of the collet 10 in an expanded, locked position. This provides a presently preferred travel of scissor grip 20 required to expand and contract the collet 10. In this embodiment, the inward bias of fingers 38 is selected to produce the desired friction, while allowing operation of the handle 23 with only one hand. Alternative taper angles of conical portion 52 and inner finger 38 surfaces, and alternative finger 38 resiliencies may be chosen according to the purposes of other embodiments.

The tissue protector 14 is preferably sized so that once the plate 56 is properly positioned over the implantation site and the collet 10 is locked to the plate, the tissue protector 14 extends to the outside of the patient's body. As a result, a spinning bit 16 will not laterally reach or harm surrounding tissues that the surgeon does not intend to drill.

Also, the handle 23 is preferably located remotely from the drilling site. This frees space near the plate 56 and permits insertion of the drill guide into narrow incisions.

Various changes to the above description are possible without departing from the scope of the invention. For example, in embodiments for use with plates that have noncircular screw holes, the outer cross-section of collet 10 may match the shape of the holes. It is intended that the following claims cover all modifications and embodiments that fall within the true spirit and scope of the present invention.

We claim:

1. Instrumentation for osteofixation comprising:

a bone plate with *a* plate hole for receiving a bone fastener and having an inner wall; and a surgical drill guide comprising *a* guide member, for guiding a drill bit, and a hollow collet disposed substantially coaxially with the guide member and having a radially expandable forward end with a radially expandable neck and an outwardly projecting rim disposed forward of the neck, the rim being configured and dimensioned such that it is freely extractable through the plate hole in a contracted collet position and impassable through the plate hole in an expanded collet position, the neck being configured and dimensioned for pressing outwardly against an inner wall of the plate hole in the expanded collet position for [releasibly] *releasably* securing the drill guide to the plate.

2. The instrumentation of claim 1, wherein the plate hole has a preselected hole diameter, and the rim defines an outer rim diameter that is smaller than the hole diameter in the contracted collet position and larger than the hole diameter in the expanded collet position.

3. The instrumentation of claim 2, wherein the collet forward end comprises a plurality of longitudinally extending fingers that define the neck and rim and that are biased radially outwardly when the guide sleeve is moved into a forward position.

4. The instrumentation of claim 2, wherein the neck and rim have an axis and the rim has a rounded cross section in a plane extending through the axis for preventing the rim from catching on the plate during extraction of the rim from the plate hole.

5. The instrumentation of claim 4, wherein the rounded cross-section of the rim has a radius of about 0.15 mm.

6. The instrumentation of claim 2, wherein the rim has a surface substantially adjacent the neck and configured at a first angle thereto of less than about 55°.

7. The instrumentation of claim 6, wherein the first angle is about 45°.

8. The instrumentation of claim 1, wherein the guide member comprises a guide sleeve disposed movably axially and telescopically within the collet and defining a guide bore for axially receiving and guiding a drill bit, the guide sleeve having a first position within the collet in which the sleeve biases the collet towards the expanded collet position.

9. The instrumentation of claim 8, wherein the sleeve has a surface tapered inwardly at a second angle of between 3° and 5° for cooperatively biasing the collet towards the expanded collet position when the [collet] *sleeve* is moved forward therein.

10. The instrumentation of claim 9, wherein the second angle is about 4°.

11. Instrumentation for osteofixation comprising:

a bone plate with *a* plate hole for receiving a bone fastener and having an inner wall of a preselected hole diameter; and a surgical drill guide comprising *a* guide member, for guiding a drill bit, and a hollow collet disposed substantially coaxially with the guide member and having a radially expandable forward end with a radially expandable neck and an outwardly projecting rim disposed forward of the neck, the rim defining a contracted outer rim diameter that is smaller than the hole diameter in [an] *a* contracted collet position and an expanded outer rim diameter that is larger than the hole diameter in an expanded collet position such that the rim is freely extractable through the plate hole in the contracted collet position and impassable through the plate hole in the expanded collet position, the neck being configured and dimensioned for pressing outwardly against an inner wall of the plate hole in the expanded collet position for [releasibly] *releasably* securing the drill guide to the plate.

12. The instrumentation of claim 11, wherein the contracted rim diameter is at least about 0.1 mm smaller than the hole diameter.

13. The instrumentation of claim 12, wherein the contracted rim diameter is no more than about 0.3 mm smaller than the hole diameter.

14. The instrumentation of claim 13, wherein the contracted rim diameter is about 0.2 mm smaller than the hole diameter.

15. The instrumentation of claim 11, wherein the contracted rim diameter is about 95% of the hole diameter.

16. The instrumentation of claim 11, wherein the rim protrudes radially from the neck by less than about 0.1 mm.

17. The instrumentation of claim 16, wherein the neck has a contracted neck diameter in the contracted collet position, the contracted rim diameter being equal to the contracted neck diameter.

18. The instrumentation of claim 11, wherein the neck has a diameter when the neck is in the contracted collet position that is at least about 95% as large as the contracted rim diameter.

19. The instrumentation of claim 11, wherein the collet is configured for naturally and resiliently biasing the rim to the contracted collet position.

20. The instrumentation of claim 11, wherein the collet comprises a shoulder having a diameter larger than the hole diameter, the shoulder, neck, and rim being a single piece of unitary construction.

21. Instrumentation for osteofixation comprising:

a locking bone plate with a plurality of plate holes for receiving [a] an anchor screw therethrough and having an inner wall of a preselected hole diameter; and a surgical drill guide comprising *a* guide member, for guiding a drill bit, and a hollow collet disposed substantially coaxially with the guide member and having a radially expandable forward end with a radially expandable neck and an outwardly projecting rim disposed forward of the neck, the rim defining a contracted outer rim diameter that is smaller than the hole diameter in [an] *a* contracted collet position and an expanded outer rim diameter that is larger than the hole diameter in an expanded collet position such that the rim is freely extractable through the plate hole in the contracted collet position and unreceivable through the plate hole in the expanded collet position, the neck being configured and dimensioned for pressing outwardly against an inner wall of the plate hole in the expanded collet position for [releasibly] *releasably* securing the drill guide to the plate hole in precise alignment therewith.

*22. Instrumentation for osteofixation comprising:*

*a bone plate with a plate hole for receiving a bone fastener and having an inner wall; and*

*a surgical drill guide comprising a guide member for guiding a drill bit, and a hollow collet disposed substantially coaxially with the guide member and having a forward end that includes a radially expandable neck which is configured and dimensioned such that the neck is freely extractable through the plate hole in a contracted collet position, the neck being configured and dimensioned for pressing outwardly against an inner wall of the plate hole in an expanded collet position for releasably securing the drill guide to the plate.*

*23. The instrumentation of claim 22, wherein the plate hole has a preselected hole diameter, and the neck has a neck diameter that is smaller than the hole diameter in the contracted collet position, and the neck diameter is expanded in the expanded collet position.*

*24. The instrumentation of claim 22, wherein the guide member comprises a guide sleeve disposed movably axially and telescopically within the collet and defining a guide bore for axially receiving and guiding a drill bit, the guide sleeve having a first position within the collet in which the sleeve biases the collet towards the expanded collet position.*

*25. The instrumentation of claim 24, wherein the sleeve has a surface tapered inwardly at an angle of between 3° and 5° for cooperatively biasing the collet towards the expanded collet position when the sleeve is moved forward therein.*

* * * * *